(12) United States Patent
Saleh et al.

(10) Patent No.: US 10,832,895 B2
(45) Date of Patent: Nov. 10, 2020

(54) STAND ALONE MICROFLUIDIC ANALYTICAL CHIP DEVICE

(71) Applicant: Plasmotica, LLC, Woodbridge, CT (US)

(72) Inventors: Nedal Saleh, Santa Clara, CA (US);
Waqas Khalid, Berkeley, CA (US);
Faisal Saleh, Woodbridge, CT (US)

(73) Assignee: Plasmotica, LLC, Woodbridge, CT (US)

( * ) Notice: Subject to any disclaimer, the term of this patent is extended or adjusted under 35 U.S.C. 154(b) by 0 days.

(21) Appl. No.: 15/600,606

(22) Filed: May 19, 2017

(65) Prior Publication Data

US 2017/0333894 A1  Nov. 23, 2017

Related U.S. Application Data

(60) Provisional application No. 62/338,955, filed on May 19, 2016, provisional application No. 62/338,996, (Continued)

(51) Int. Cl.
*H01J 37/32* (2006.01)
*B01F 13/00* (2006.01)
(Continued)

(52) U.S. Cl.
CPC ...... *H01J 37/3233* (2013.01); *B01F 13/0064* (2013.01); *B01J 19/0093* (2013.01);
(Continued)

(58) Field of Classification Search
None
See application file for complete search history.

(56) References Cited

U.S. PATENT DOCUMENTS 4,509,451 A   4/1985  Collins et al.
5,070,282 A  12/1991  Epsztein
(Continued)

FOREIGN PATENT DOCUMENTS

WO   2010146153 A1  12/2010
WO   2012154306 A1  11/2012
(Continued)

OTHER PUBLICATIONS

3D Nanoprototyping with a DualBeam, www.fei.com/documents/3d-nanoprototyping-with-a-dualbeam, 2013, pp. 1 to 12.
(Continued)

*Primary Examiner* — Xiaoyun R Xu
(74) *Attorney, Agent, or Firm* — Pillsbury Winthrop Shaw Pittman, LLP

(57) ABSTRACT

Provided is an analytical device including: a self-flowing microfluidic system, having a sample extraction location, at least one sample preparation location, and at least one sample analytical chamber; wherein the sample extraction location, the sample preparation location, and the at least one sample analytical chamber are interconnected by at least one microfluidic channel on a first substrate; and a signal readout system, having at least one sample analysis elements, and a data gathering and processing element.

19 Claims, 4 Drawing Sheets

Related U.S. Application Data filed on May 19, 2016, provisional application No. 62/339,002, filed on May 19, 2016, provisional application No. 62/339,008, filed on May 19, 2016.

(51) Int. Cl.

| | |
|---|---|
| *B01L 3/00* | (2006.01) |
| *B01J 19/00* | (2006.01) |
| *C12Q 1/6837* | (2018.01) |
| *G01N 1/38* | (2006.01) |

(52) U.S. Cl.
CPC ......... *B01L 3/5023* (2013.01); *B01L 3/5027* (2013.01); *B01L 3/502715* (2013.01); *B01L 3/502753* (2013.01); *C12Q 1/6837* (2013.01); *H01J 37/3244* (2013.01); *H01J 37/3299* (2013.01); *H01J 37/32366* (2013.01); *H01J 37/32733* (2013.01); *B01J 2219/00781* (2013.01); *B01J 2219/00869* (2013.01); *B01L 2200/06* (2013.01); *B01L 2300/0645* (2013.01); *B01L 2300/0654* (2013.01); *B01L 2300/0681* (2013.01); *B01L 2300/1827* (2013.01); *B01L 2400/0688* (2013.01); *G01N 1/38* (2013.01); *H01J 2237/327* (2013.01); *H01J 2237/334* (2013.01)

(56) References Cited

U.S. PATENT DOCUMENTS

| | | | |
|---|---|---|---|
| 5,230,866 | A | 7/1993 | Shartle et al. |
| 5,294,465 | A | 3/1994 | Gallagher |
| 5,587,586 | A | 12/1996 | Kruit |
| 6,787,122 | B2 | 9/2004 | Zhou |
| 7,220,971 | B1 | 5/2007 | Chang et al. |
| 7,791,055 | B2 | 9/2010 | Williamson et al. |
| 2002/0187556 | A1 | 12/2002 | Shartle et al. |
| 2003/0038244 | A1 | 2/2003 | Thomas et al. |
| 2003/0052096 | A1 | 3/2003 | Crowe et al. |
| 2004/0091399 | A1 | 5/2004 | Chung et al. |
| 2004/0115831 | A1* | 6/2004 | Meathrel .......... G01N 33/54366 436/514 |
| 2004/0262540 | A1 | 12/2004 | Nagaseki et al. |
| 2006/0103035 | A1 | 5/2006 | Maruyama |
| 2006/0208649 | A1 | 9/2006 | Rueger et al. |
| 2008/0067421 | A1 | 3/2008 | Cheng |
| 2008/0212216 | A1* | 9/2008 | Milosevic ............ G02B 17/004 359/850 |
| 2008/0283767 | A1 | 11/2008 | Platzgummer |
| 2008/0318334 | A1* | 12/2008 | Robotti .............. G01N 30/6095 436/161 |
| 2009/0044875 | A1 | 2/2009 | Griss et al. |
| 2009/0281650 | A1 | 11/2009 | Kassab |
| 2010/0105577 | A1 | 4/2010 | Dugan et al. |
| 2010/0200094 | A1 | 8/2010 | Ermakov |
| 2012/0003394 | A1 | 1/2012 | Mulders et al. |
| 2012/0045863 | A1 | 2/2012 | Hopwood |
| 2012/0123686 | A1* | 5/2012 | Xiang ................... G16H 40/63 702/19 |
| 2013/0098551 | A1 | 4/2013 | Dort et al. |
| 2013/0206720 | A1 | 8/2013 | Blom et al. |
| 2014/0303037 | A1 | 10/2014 | Short et al. |
| 2014/0377146 | A1 | 12/2014 | Putnam et al. |
| 2015/0290669 | A1 | 10/2015 | Li et al. |
| 2016/0299103 | A1 | 10/2016 | Saleh et al. |
| 2017/0098557 | A1 | 4/2017 | Shimizu et al. |
| 2017/0307601 | A1 | 10/2017 | Putnam et al. |
| 2017/0365438 | A1 | 12/2017 | Akinwande et al. |

FOREIGN PATENT DOCUMENTS

| | | | | |
|---|---|---|---|---|
| WO | WO 2012/154306 | * | 11/2012 | .......... G01N 33/543 |
| WO | 2015/051175 A2 | | 4/2015 | |
| WO | 2015137364 A1 | | 9/2015 | |
| WO | 2017201505 A3 | | 11/2017 | |

OTHER PUBLICATIONS

A rapid, inexpensive surface treatment for enhanced functionality of polydimethylsiloxane microfluidic channels, www.ncbi.nlm.nih.gov/pmc/articles/PMC3423308, Jul. 30, 2012, pp. 1 to 12.

Electron beam-induced deposition, Wikipedia, https://en.wikipedia.org/wiki/Electron_beam-induced_deposition, Feb. 20, 2016, pp. 1 to 5.

Electron-beam-induced deposition with carbon nanotube emitters, www.egr.msu.edu/~dong/Publication/JP200203_APL_81_1919_Dong.pdf, Applied Physics Letters vol. 81, No. 10, Sep. 2, 2002, pp. 1 to 3.

Fabrication and characterization of nanostructures on insulator substrates by electron-beam-induced deposition, IIOP Publishing, Sci. Technol. Adv. Mater. 9 (2008) 023002 (10pp), http://www.tandfonline.com/doi/full/10.1088/1468-6996/9/2/023002, Aug. 1, 2008, pp. 1 to 11.

Fabrication and Functionalization of Nanochannels by Electron-Beam-Induced Silicon Oxide Deposition, http://pubs.acs.org/doi/abs/10.1021/Ia061321c, Sep. 6, 2006, pp. 1 to 4.

Hydrophilic Surface Modification of PDMS Microchannel for O/W and W/O/W Emulsions, www.mdpi.com/journal/micromachines, Sep. 29, 2015, pp. 1 to 14.

Integration of microplasma and microfluidic technologies for localised microchannel surface modification, Proceedings vol. 8204, SPIE Smart Nano, Micro Materials and Devices, Dec. 4-7, 2011, pp. 1 to 7.

Ion-Enhanced Field Emission for Control of Atmospheric Pressure Discharges, Aerospace and Mechanical Engineering Chemical and Biomolecular Engineering University of Notre Dame, http://www.nd.edu/~sst, Jun. 25, 2014, pp. 1 to 28.

Microfluidics Meets MEMS, Proceedings of the IEEE, vol. 91, No. 6, Jun. 2003, www-mtl.mit.edu/researchgroups/mems-salon/Hongwei_microfluidicMEMS.pdf, Apr. 4, 2003, pp. 1 to 24.

Microplasma, Wikipedia, https://en.wikipedia.org/wiki/Microplasma, Oct. 22, 2015, pp. 1 to 10.

Microplasma-Based Treatment of Inner Surfaces in Microfluidic Devices,www.altmetric.com/details.php?domain=onlinelibrary.wiley.com&doi=10.1002%2Fctpp.200710008, Feb. 1, 2007, pp. 1 to 3.

Multibeam Electron Source using MEMS Electron Optical Components, Journal of Physics: Conference Series 34, International MEMS Conference 2006, http://iopscience.iop.org/article/10.1088/1742-6596/34/1/180/pdf, pp. 1 to 6.

Nanofabrication by advanced electron microscopy using intense and focused beam, IOP Publishing, Sci. Technol. Adv. Mater. 9 (2008) 014110 (20pp), http://iopscience.iop.org/article/10.1088/1468-6996/9/1/014110/meta, May 27, 2008, pp. 1 to 21.

Oxygen plasma treatment for reducing hydrophobicity of a sealed polydimethylsiloxane microchannel, http://www.ncbi.nlm.nih.gov/pmc/articles/PMC2967237/, Sep. 30, 2010, pp. 1 to 8.

Parallel electron-beam-induced deposition using a multi-beam scanning electron microscope, J. Vac. Sci. Technol. B, vol. 29, No. 6, Nov./Dec. 2011, http://avs.scitation.org/doi/abs/10.1116/1.3656027, Oct. 26, 2011, pp. 1 to 4.

Review article: Fabrication of nanofluidic devices, Biomicrofluidics 7, 026501 (2013), American Institute of Physics, http://dx.doi.org/10.1063/1.4794973, Mar. 13, 2013, pp. 1 to 41.

Surface patterning of bonded microfluidic channels, Biomicrofluidics. Sep. 2010; 4(3): 032206, American Institute of Physics, http://dx.doi.org/10.1063/1.3493643, Sep. 30, 2010, pp. 1 to 14.

Surface Technology with Cold Microplasmas, Plasma Processes and Polymers, vol. 4, Issue 3, Apr. 23, 2007, http://onlinelibrary.wiley.com/doi/10.1002/ppap.200600116/full, pp. 1 to 5.

(56) References Cited

OTHER PUBLICATIONS

Surface-Tension-Confined Microfluidics and Their Applications, ChemPhysChem 2013, https://www.researchgate.net/publication/234099281, Feb. 2013, pp. 1 to 12.
What is the difference between SEM and FESEM?, ResearchGate, www.researchgate.net/post/What_is_the_difference_between_SEM_and_FESEM, Dec. 20, 2013, pp. 1 to 5.
Micro Systems and Devices for (Bio)chemical Processes, https://books.google.com/books?id=bt3Sd8H0XXAC, Academic Press as in imprint of Elsevier, 2010, pp. 1 to 1.
Related PCT Application No. US2017/033695 filed on May 19, 2017, pp. 1 to 48.
International Search Report and Written Opinion for Related PCT Application No. PCT/US2017/033695 dated Nov. 29, 2017, pp. 1 to 25.
Related U.S. Appl. No. 15/630,095, filed Jun. 22, 2017, pp. 1 to 48.
Restriction Requirement for Related U.S. Appl. No. 15/630,095 dated Sep. 1, 2017, pp. 1 to 10.
Non-Final Office Action for Related U.S. Appl. No. 15/630,095 dated Dec. 29, 2017, pp. 1 to 26.
Final Office Action for Related U.S. Appl. No. 15/630,095 dated May 3, 2018, pp. 1 to 65.
Related U.S. Appl. No. 15/600,492, filed May 19, 2017, pp. 1 to 48.
Non-Final Office Action for Related U.S. Appl. No. 15/600,492 dated Nov. 1, 2017, pp. 1 to 27.
Restriction Requirement for Related U.S. Appl. No. 15/600,492 dated Jun. 15, 2018, pp. 1 to 6.
Related U.S. Appl. No. 15/630,137, filed Jun. 22, 2017, pp. 1 to 48.
Restriction Requirement for Related U.S. Appl. No. 15/630,137 dated Aug. 2, 2017, pp. 1 to 9.
Non-Final Office Action for Related U.S. Appl. No. 15/630,137 dated Oct. 31, 2017, pp. 1 to 18.
Final Office Action for Related U.S. Appl. No. 15/630,137 dated May 14, 2018, pp. 1 to 17.
Non-Final Office Action for Related U.S. Appl. No. 15/630,137 dated Dec. 12, 2018, pp. 1 to 20.
Related U.S. Appl. No. 15/630,164, filed Jun. 22, 2017, pp. 1 to 48.
Non-Final Office Action for Related U.S. Appl. No. 15/630,164 dated Aug. 14, 2017, pp. 1 to 10.
Noblitt, S.D. et al., "Integrated Membrane Filters for Minimizing Hydrodynamic Flow and Filtering in Microfluidic Devices", 2007, Analytical Chemistry, vol. 79(16), pp. 6249-6254.
Final Office Action for Related U.S. Appl. No. 15/630,164 dated Dec. 18, 2017, pp. 1 to 10.
Tachibana, H. et al. "Self-propelled continuous-flow PCR in capillary-driven microfluidic device: Microfluidic behavior and DNA amplification", 2015, Sensors and Actuators B vol. 206, pp. 303-310.
Zhu, Y. et al , "Capillary flow in microchannels", 2010, Microfluid Nanofluid, vol. 8, pp. 275-282.
Non-Final Office Action for Related U.S. Appl. No. 15/630,164 dated Aug. 28, 2018, pp. 1 to 10.
Non-Final Office Action for Related U.S. Appl. No. 15/600,470, dated Jan. 30, 2019, pp. 1 to 26.
Final Office Action for Related US Patent Application , dated Mar. 13, 2019, pp. 1 to 37.
Khademhosseini, A. et al., "A Soft Lithographic Approach to Fabricate Patterned Microfluidic Channels, Analytical Chemistry," vol. 76, 2004, pp. 3675-3681.
Final Office Action for Related U.S. Appl. No. 15/630,164, dated Mar. 13, 2019, pp. 1 to 37.
International Preliminary Report on Patentability for Related PCT Application No. PCT/US2017/033695, dated Nov. 29, 2018, pp. 1 to 19.
Final Office Action for Related U.S. Appl. No. 15/630,137 dated Aug. 30, 2019, pp. 1 to 16.
Non-Fina Office Action for Related U.S. Appl. No. 15/600,492 dated Sep. 27, 2019, pp. 1 to 14.
Non-Final Office Action for Related U.S. Appl. No. 15/630,164, dated Sep. 12, 2019, pp. 1 to 10.
Non-Final Office Action for Related U.S. Appl. No. 15/630,095, dated Dec. 12, 2019, pp. 1 to 47.
Final Office Action for related U.S. Appl. No. 15/630,164, dated Dec. 31, 2019, pp. 1 to 26.
Kim, S.C. et al, "Lab on a Chip: Patterning microfluidic device wettability with spatially-controlled plasma oxidation," vol. 15, 2015, pp. 1 to 7.

\* cited by examiner

STAND ALONE MICROFLUIDIC ANALYTICAL CHIP DEVICE

CROSS-REFERENCE TO RELATED APPLICATIONS

The present patent filing claims the benefit of U.S. Provisional Patent Application 62/338,955, titled APPARATUS AND METHOD FOR PROGRAMMABLE SPATIALLY SELECTIVE NANOSCALE SURFACE FUNCTIONALIZATION, filed 19 May 2016; U.S. Provisional Patent Application 62/338,996, titled PUMP-FREE MICROFLUIDIC ANALYTICAL CHIP, filed 19 May 2016; U.S. Provisional Patent Application 62/339,002, titled PUMP-FREE MICROFLUIDIC ANALYTICAL SYSTEMS, filed 19 May 2016; and U.S. Provisional Patent Application 62/339,008, titled STAND ALONE PUMP-FREE MICROFLUIDIC ANALYTICAL CHIP DEVICE, filed 19 May 2016. The content of each of these earlier filed patent applications is hereby incorporated by reference in its entirety.

FIELD OF THE INVENTION

The present disclosure related to point of care diagnostic devices, medical testing devices, in vitro testing, and systems for collecting and displaying analytical testing data.

BACKGROUND OF THE INVENTION

Microfluidic devices provide significant flexibility to persons performing testing of samples because microfluidic devices may accept and process sample sizes significantly smaller than those of traditional chemical assays. In vitro and point-of-care testing of biological samples may become less expensive by further reducing a sample size of a microfluidic analytical chip.

SUMMARY OF THE INVENTION

Some aspects include an analytical device comprising: a self-flowing microfluidic system, having a sample extraction location, at least one sample preparation location, and at least one sample analytical chamber; wherein the sample extraction location, the sample preparation location, and the at least one sample analytical chamber are interconnected by at least one microfluidic channel on a first substrate; and a signal readout system, having at least one sample analysis elements, and a data gathering and processing element.

Some aspects include an analytical device comprising: a signal readout system, having a card reader slot, at least one sample analysis element, and a data gathering and processing element, wherein plurality of sample analysis detection elements, the data processing element and the data transmission element are communicatively connected by a communication element, and wherein the card reader slot is configured to accept a test card comprising a pump-free microfluidic system, having a sample extraction location, at least one sample preparation location, and at least one sample analytical chamber; wherein the sample extraction location, the sample preparation location, and the at least one sample analytical chamber are interconnected by at least one microfluidic channel on a first substrate.

Some aspects include an arrangement comprising: a signal readout system, having a card reader slot, at least one sample analysis element, and a data gathering and processing element, wherein plurality of sample analysis detection elements, the data processing element and the data transmission element are communicatively connected by a communication element, and wherein the card reader slot is configured to accept a test card comprising a pump-free microfluidic system, having a sample extraction location, at least one sample preparation location, and at least one sample analytical chamber; wherein the sample extraction location, the sample preparation location, and the at least one sample analytical chamber are interconnected by at least one microfluidic channel on a first substrate.

BRIEF DESCRIPTION OF THE DRAWINGS

The invention is illustrated by way of example, and not by way of limitation, in the figures of the accompanying drawing and in which like reference numerals refer to similar elements.

DETAILED DESCRIPTION OF THE INVENTION

Figure 1:
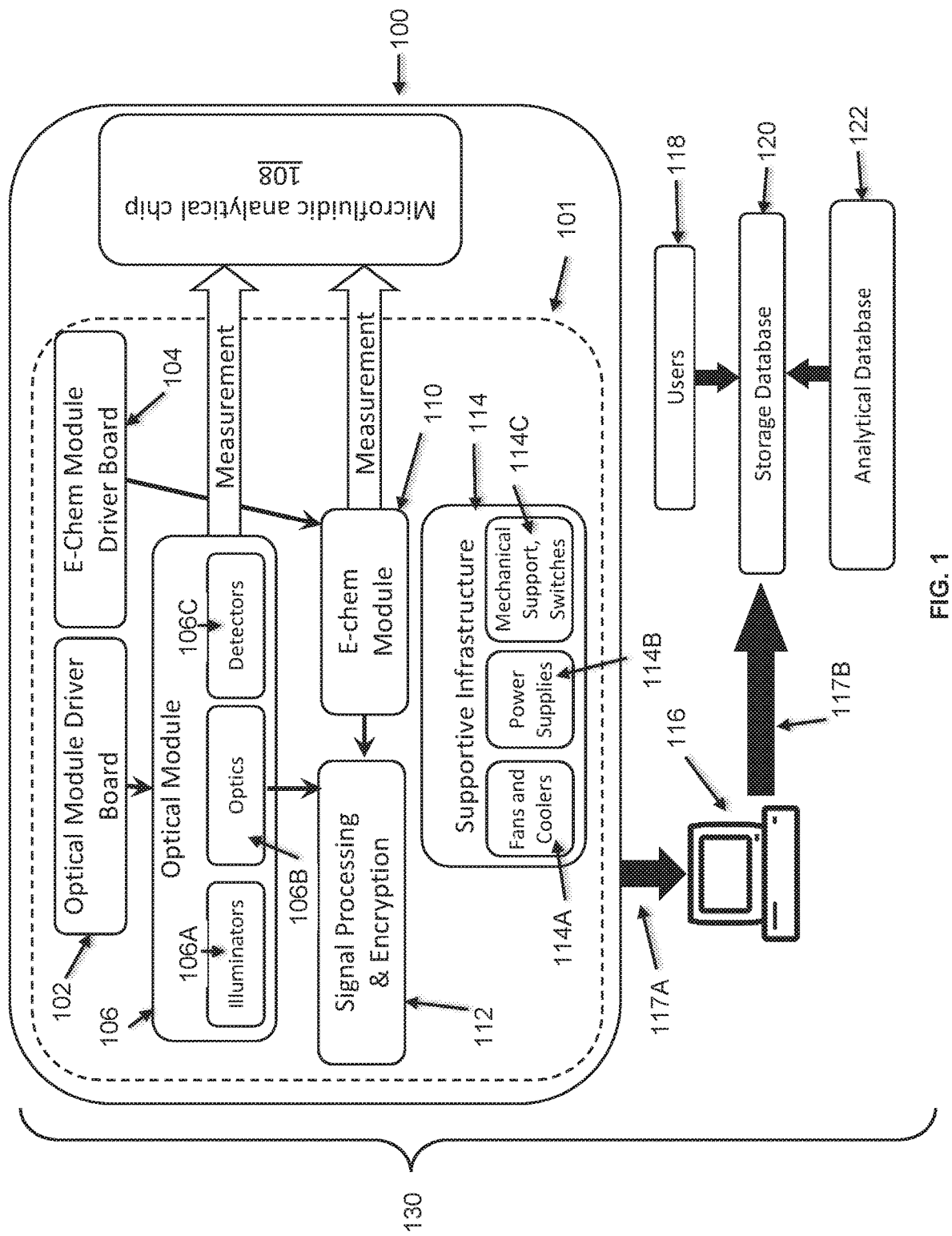
FIG. 1 depicts an embodiment of a microfluidic chip testing device.

Microfluidic devices have become increasingly popular in point-of-care diagnostics and in vitro testing of samples because of the reduced sample size associated with using a microfluidic chip in a testing scenario. Smaller sample sizes are associated with lower cost testing because smaller sample sizes involve a reduction in the quantity of chemical reagents in performing chemical assays, and involve faster processing time for obtaining results from analysis of samples using the microfluidic chip. Microfluidic analytical chip testing may be more convenient for a user because the testing equipment may be smaller than laboratory equipment associated with traditional laboratory test methods.

Microfluidic chips may contain, in reservoirs on the microfluidic chip, chemical reagents associated with performing a chemical test or assay. Some embodiments of microfluidic chips may be used and discarded after testing by a chip reader configured to receive, and interconnect with, microfluidic chips inserted therein. A microfluidic analytical chip may reduce total cost of chemical reagents (because smaller quantities may be used), greater portability, cleaner testing conditions (chips may be sealed, and then opened on an as-needed basis), and more rapid testing results because of progress in testing device automation.

Convenience and desirability of using microfluidic chips for chemical assays may be further increased by providing a portable microfluidic chip analyzer or reader device which can interface with electrical connections or optical windows of the microfluidic chip. Portable microfluidic chip systems may have portable power reserves, and may have economies of scale associated with inexpensive testing.

Further, developments in wireless communication and users' increasing comfort with using portable electronics to consume and interact with collected electronic data may further promote the desirability of portable microfluidic chip reading devices. In an embodiment, an integrated microfluidic chip testing device, having a microfluidic chip embedded in a single use testing card, may prove popular for users in outdoor or field conditions, where consistent power supplies and data connections may be irregular.

A microfluidic chip may include a first substrate that has been processed in order to contain a plurality of microfluidic channels. Microfluidic channels may be pressed into a top surface of the substrate, etched into the substrate by removing substrate material, or may be formed on a flat top surface of the substrate by functionalization of the top surface using, e.g., a plasma process that induces a chemical change in the substrate surface. Surface functionalization may improve a performance characteristic (such as evaporation loss) of recessed microfluidic channels. A chemical change in the substrate surface may promote spontaneous movement of a fluid across the top of the substrate without use of external pressure, pumps, or other devices to move fluid through the microfluidic channels. Fluid handing equipment associated with pump-driven microfluidic testing may be omitted from analytical chip testing systems that employ microfluidic analytical chips having self-flowing (or, spontaneously flowing) microfluidic channels.

A microfluidic chip may include a sample extraction location, a sample preparation location, and sample analysis locations interconnected by the microfluidic channels. Microfluidic channels may be portions of a substrate top surface that have been modified to have greater attraction to a component of a sample. In an embodiment, a microfluidic chip may be made of a polymeric substance such as polymethylmethacrylate (PMMA) having a pattern of enhanced hydrophilicity (caused by more oxygen on a substrate surface) on the top surface formed by plasma processing a plurality of patterned regions to form microfluidic channels.

Sample extraction locations of the microfluidic chip may be configured to direct a fluid applied to an opening of the sample extraction location into one or more of the microfluidic channels in the microfluidic chip. Sample extraction locations may include arrays of microneedles, or recesses into which a fluid may be added by, e.g., insertion from a syringe containing a fluid example, or placing a drop of fluid example on the surface extraction location opening.

A microfluidic chip may conclude a plurality of sample preparation locations including one or more of reagent chambers for holding chemical reagents, membrane chambers and filter chambers for separating components a fluid example, micrometer chambers for maintaining a temperature of a sample or heating a sample to promote a chemical reaction, fluid mixing chambers fluid separation chambers, and chambers for performing chromatographic separation.

Sample preparation locations may be quick used singly, or in groups, in order to prepare a volume of fluid example for analysis in a sample analysis location of the microfluidic chip. Sample analysis locations may include sample analysis elements such as electrochemical analysis chambers, optical analysis chambers, biomaterial analysis chambers, or spectrophotometry chambers. In some embodiments, a fluid example may be divided into multiple volumes prepared in similar fashions but directed to different sample analysis locations to ascertain a variety of analytical results on sample volumes that have been prepared in a similar manner.

One desirable feature of portable microfluidic analytical chip reader devices may be the ability to use a microfluidic analytical chip in a portable reader device without resorting to the use of external pressure, external pumping systems, or fluid reservoirs in order to move portions of the fluid example through a microfluidic analytical chip. A microfluidic analytical chip that has been generated by functionalizing surfaces of the analytical chip to undergo self-displacement through the microfluidic chip may significantly reduce the weight, the size, and power specifications associated with microfluidic analytic chip testing in a portable reader device. In an embodiment of a microfluidic analytic chip reader device configured to receive pump-free microfluidic analytical chips, a power supply, optical illuminators, filtering and collection optics, and detectors, and electrochemical module driver boards may be included in a single-use or disposable reader device having a self-contained, non-removable microfluidic analytical chip.

FIG. 1 depicts an embodiment of a microfluidic chip testing device (an analytical device) 100, outlining subsystems and components of the testing device that perform various testing functions. Analytical device comprises an optical module driver board 102, and electrochemical module driver board 104, an optical module 106 for generating filtering and detecting light, a signal processing and encryption module 112, and electrochemical module 110 for interpreting signals generated at electrodes within a test card or microfluidic analytical chip 108 inserted into the analytical device 100. Analytical device 100 further includes supporting infrastructure 114 which may include cooling devices, a power supply, structural support, and interactive elements configured to receive input from a user and to provide output to a user. Analytical device 100 may include a power connection bus (not shown) configured to interconnect modules of the analytical device (e.g., optical module, optical module driver board 102, electrochemical module driver board 104, electrochemical module 110, or signal processing and encryption module 112) for purposes of providing power and receiving data from analytical chambers of the analytical device.

Analytical device 100 may transmit, from signal processing and encryption module 112, to an external computing device 116, information regarding analytical results collected by analytical device 100 from volumes of fluid example processed through microfluidic analytical chip 108. External computing device 116 may include an input/output module for communicating with the analytical device and with external databases such as external storage database 120. External computing device may include a mode of entering information to communicate with an analytical device, as well as a mode of adjusting the presentation of information from the external computing device to a user or to an external storage database 120.

Microfluidic analytical chip 108 may include a number of preloaded chemicals stored in sample preparation locations awaiting the introduction of a fluid example through a sample extraction location of the microfluidic analytical chip. Microfluidic analytical chip 108 may be, in some embodiments, inserted and removed from the analytical device 100. Analytical device 100 may be mechanically isolated and sealed to form a light proof seal to promote accurate optical testing results.

Upon insertion of microfluidic analytical chip 108 into analytical device 100, and formation of a light proof seal, illuminators 106A may generate an optical signal transmitted through filtering and collection optics 106B of the optical module into detectors 106C. An optical path of the optical signal may extend through optical analysis chambers located in microfluidic analytical chip 108. Of light from optical module 106 may shine through an optical analytical chamber. In some embodiments, a path for detection of light from an optical analytical chamber may be perpendicular to a path for light transmission through the optical analytical chamber. An optical module driver board may be configured to regulate light intensity, a selection of illuminators 106A turned on during a particular microfluidic test process, and may perform signal processing and encryption of data from a subset of the optical pathways present in the analytical device. Optical module 106 may operate in different modes, according to an operational parameter transmitted to the optical module. Some modes may involve performing fluorimetry on a fluidic sample. Some modes may involve absorption spectroscopy. Some optical module operational modes may involve other optical analytical techniques compatible with small sample sizes, where light from an optical source passes through a fluidic sample in a single pass. Some optical module operational modes involve passing light form the optical source through a sample two or more times, increasing the magnitude of a signal for the optical test. In some embodiments, a user may indicate to the analytic device a type of optical test to be performed using an external computing device 116 to program the analytical device. In some embodiments, a testing card having a microfluidic analytical chip incorporated therein may be configured to contain and transmit an instruction about what optical mode(s) can be performed using a microfluidic analytical chip (i.e., not all chips may be able to perform all test, so an instruction from the chip to the analytical device may communicate regarding what optical cells may be available, what wavelengths to use, a duration of a test, etc. . . . ).

Electrochemical module driver board 104 may be configured to detect an analytical signal being generated by an electrochemical analysis chamber in microfluidic analytical chip 108. Electrochemical module driver board 100 for me also be configured to instruct signal processing and encryption module 112 to receive, from electrochemical module 110, signals generated by microfluidic analytical chip 108 during a testing process.

Optical module 106 may include detectors 106C configured to detect the presence of biomarkers or other components of a fluid example down to concentrations of 1 picomol/liter (pmol/l), and up to 1000 micromol/liter (μmol/l), according to embodiments analytical device 100 may be configured to scale with different sizes of fluid examples according to a number of tests directed to be performed on the fluid sample during an analytical process. According to an embodiment, the electrochemical module may be configured to detect currents from electrodes in the microfluidic analytical chip ranging from approximately one picoamp (pA)21 milliamp (mA).

According to an embodiment, supporting infrastructure 114 of analytical device 100 may receive input from user and display output to user. In an embodiment, the input and output may include information regarding test results from microfluidic analytical chip 108. External computing device 116 may be configured, upon receipt of information regarding test results from the analytical device, to receive 117A the information the signal processing and encryption device, and to transmit 117B the information to an external storage database 120, configured to permit users 118, or computing devices 122, to query the database, analyze the data stored therein, and process or display the testing information. Testing system 130 may be a portable system, or may be a networked system incorporated into a medical care facility.

Figure 2:
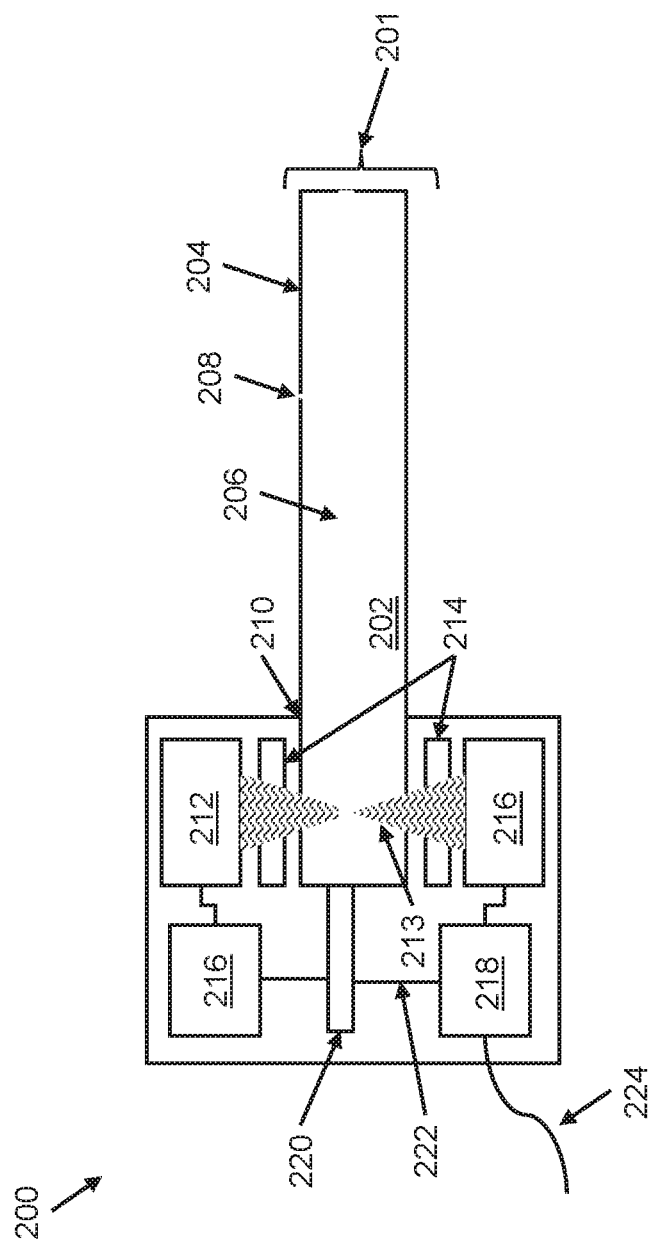
FIG. 2 depicts a cross-sectional view of a microfluidic chip testing device having a microfluidic chip test card inserted therein.
Figure 3:
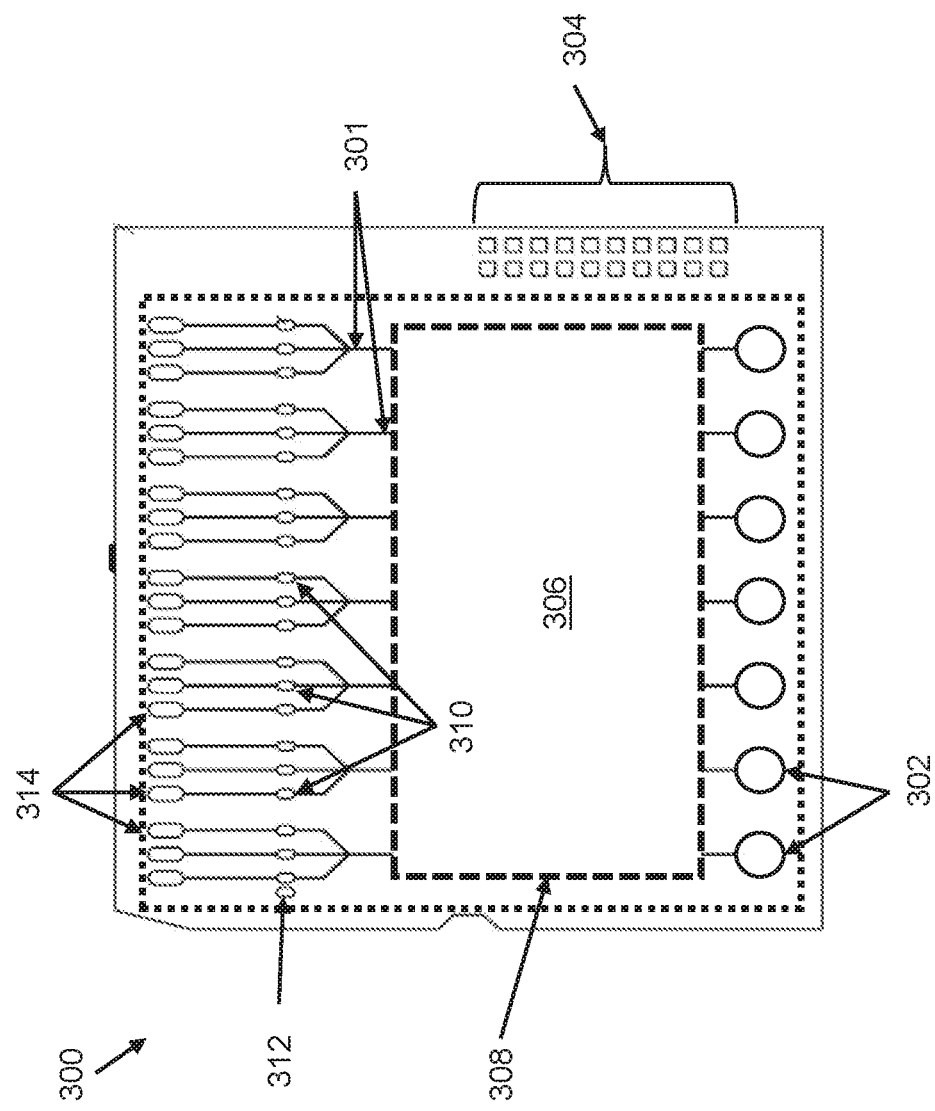
FIG. 3 depicts a top view of a microfluidic chip test card that can be inserted into a microfluidic chip testing device.

FIG. 2 depicts a stand alone testing system 200 having a microfluidic analytical chip card 201 inserted into an opening 210 of the standalone testing system. Microfluidic chip includes a first substrate 202 with a second substrate 204 located on a top side of the first substrate. Microfluidic path 206 extends between the first and second substrates, with a sample extraction location 208 in the second substrate to allow passage of a fluidic sample into the microfluidic analytical chip card 201. Standalone testing system 200 comprises an optical source 212, an optical beam 213, and an optical detector 216 positioned at a proximal end of the microfluidic analytical chip chard 210 inserted into opening 210. Optical beam 213 extends through microfluidic path 206 to extract information about the fluidic sample in the microfluidic path 206. Standalone testing system 200 also comprises filters 214 to modify optical beam 213 between optical source 212 and optical detector 216. In an embodiment, filters reduce polarization and glare from the optical source 212 on the optical detector. Standalone testing system 200 may also contain an electronics board 216 configured to communicate with, and to control, other components of the standalone testing system 200, and an input/output controller 218 to receive and to transmit a signal containing information regarding the tested fluidic sample in the microfluidic analytical chip card 201. I/O controller 218 may be electrically connected to another computing device to promote communication of data and instructions regarding operation of standalone FIG. 3 depicts microfluidic analytical chip 300. Microfluidic analytical chip 300 includes a plurality of sample preparation chambers 300 to, which may include chemical reservoirs for adding compounds to a fluid example added to the microfluidic analytical chip. The microfluidic chip may also contain a plurality of microfluidic channels 301, extending from sample preparation chambers 302 toward sample analysis chambers 310 and waste chambers 314. According to an embodiment, sample analysis chambers may include optical analysis chambers and electrochemical analysis chambers. A reference electrode chamber 312 may be located on microfluidic analytical chip 300 in order to provide a reference voltage for electrical measurements performed during analysis of a fluid example. The microfluidic chip may contain a sample preparation region 306 in which chemical treatments are performed on microfluidic sample beneath a second substrate 308 which covers sample preparation area 306 during operation of the microfluidic chip. Microfluidic analytical chip 300 may also include a plurality of measurement pads 304 four electrodes connected to sample analysis chambers 300 on the microfluidic chip. Measurement pads 304 may be configured to make electrical contact with a standalone microfluidic analytical chip device when the microfluidic analytical chip 300 is inserted into a receiving slot of the standalone analytic device.

Figure 4:
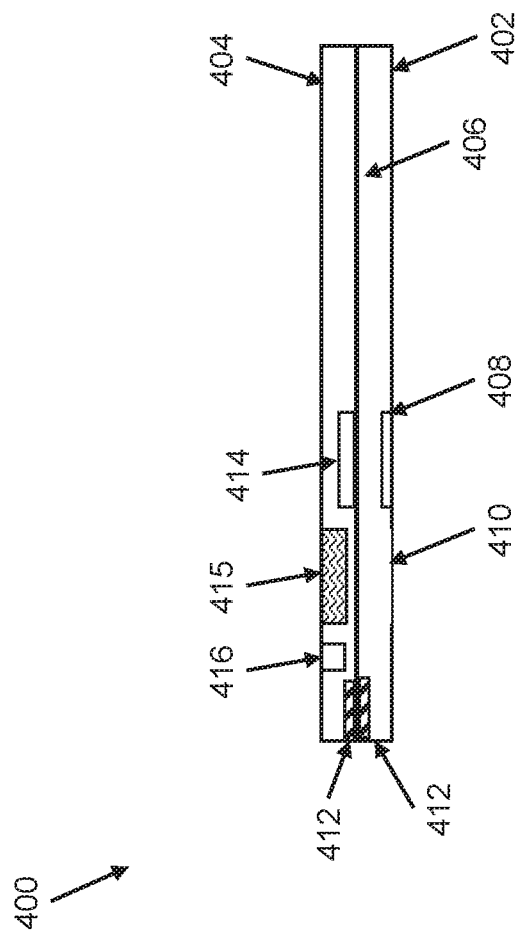
FIG. 4 depicts a cross-sectional view of a microfluidic analytical chip compatible with a standalone microfluidic analytical chip system.

FIG. 4 depicts a cross-sectional view of a microfluidic analytical chip test card 400, comprising a first substrate 402 and a second substrate 404. For some stray 402 may have imprinted thereon, a fluidic path 406 configured to process a fluid example introduced into microfluidic analytical chip test card 400. Microfluidic analytical chip test card 400 may also include a light source 414 positioned above an optical detector 408 such that a portion of microfluidic path 406 extends between light source 414 and optical detector 408. Microfluidic analytical chip test card 400 may further include an electrochemical detector 410 positioned to make contact with a portion of microfluidic path 406 during operation of the analytical chip test card. Microfluidic analytical chip test card 400 may include, in some embodiments, an independent power supply, or battery 414, a data-gathering and processing element 415, and a communication device 416. In an embodiment, communication device 416 may be a wired communication device configured to make direct flex contract with a portion of a microfluidic analytical chip device. In an embodiment, education device 416 may be an RFID or wireless education device configured to transmit an electromagnetic signal to a receiving station in an analytical device or in an external computing device. Microfluidic analytical chip test card 400 may also include a plurality of electrical contacts 412 figured to make electrical contact with power or communication elements of a standalone microfluidic analytical chip device into which the analytical test card is inserted.

According to an embodiment, optical source 414 may be a light emitting diode, a laser, or some other light source, including a solid state light source embedded into analytical chip test card 400. In an embodiment, optical detector 408 and electrochemical detector 410 may make direct electrical contact with a standalone microfluidic analytical chip device to transmit test data.

In some embodiments, the analytical system described herein may operate upon an analytical chip like that described in a U.S. Patent Application titled SELF-FLOWING MICROFLUIDIC ANALYTICAL CHIP filed on the same day as this patent filing, the contents of which are incorporated by reference. In some embodiments, the analytical chip may be manufactured with a patterning device like that described in a U.S. Patent Application titled APPARATUS AND METHOD FOR PROGRAMMABLE SPATIALLY SELECTIVE NANOSCALE SURFACE FUNCTIONALIZATION filed on the same day as this patent filing, the contents of which are incorporated by reference.

What is claimed is:

1. An analytical device comprising:
    a signal readout system, having
        a card reader having a test card receptacle,
        at least one sample analysis element, and
        a data gathering and processing element, wherein plurality of sample analysis detection elements, the data processing element and the data transmission element are communicatively connected by a communication element, and wherein the card reader receptacle is configured to accept a test card comprising:
    a pump-free microfluidic system, having
        a sample extraction location,
        at least one sample preparation location,
        a plurality of microfluidic channels on a non-recessed surface, the plurality of microfluidic channels being defined by regions of the surface having different hydrophilicity relative to other areas of the surface, at least some of the microfluidic channels being configured to promote movement of fluid from the sample extraction location to the sample preparation location in the absence of a pressure applied to the fluid, and
        at least one sample analytical chamber comprising one or more of a electrochemical analysis chamber, an optical analysis chamber, a biomaterial analysis chamber, or a spectrophotometry chamber,
        wherein the sample extraction location, the sample preparation location, and the at least one sample analytical chamber are interconnected by at least one of the plurality of microfluidic channels on a first substrate having the surface, wherein:
            the signal readout system is configured to receive from a microfluidic analytical chip of the pump-free microfluidic system instructions specifying, at least in part, one or more optical modes of measuring the fluid and execute the instructions to measure the fluid with the one or more optical modes.

2. The analytical device of claim 1, further comprising a test card interface configured to electrically connect the communication element to an electrochemical sensor of the test card.

3. The analytical device of claim 1, further comprising a data transmission element.

4. An arrangement comprising:
    a signal readout system, having
        a card reader having a test card receptacle,
        at least one sample analysis element, and
        a data gathering and processing element, wherein plurality of sample analysis detection elements, the data processing element and the data transmission element are communicatively connected by a communication element, and wherein the card reader receptacle is configured to accept a test card comprising
    a pump-free microfluidic system, having
        a sample extraction location,
        at least one sample preparation location,
        a plurality of microfluidic channels on a flat non-recessed surface, the plurality of microfluidic channels being defined by regions of the non-recessed surface having different hydrophilicity relative to one another, at least some of the plurality of microfluidic channels being configured to promote movement of fluid from the sample extraction location to the sample preparation location in the absence of a pressure applied to the fluid, and
        at least one sample analytical chamber comprising one or more of a electrochemical analysis chamber, an optical analysis chamber, a biomaterial analysis chamber, or a spectrophotometry chamber,
        wherein the sample extraction location, the sample preparation location, and the at least one sample analytical chamber are interconnected by at least one microfluidic channel on a first substrate, wherein:
            the signal readout system is configured to receive from a microfluidic analytical chip of the pump-free microfluidic system instructions specifying, at least in part, one or more optical modes of measuring the fluid and execute the instructions to measure the fluid with the one or more optical modes.

5. The analytical device of claim 1, wherein the data gathering and processing element comprises two or more of an optical module driver board, and electrochemical module driver board, an optical filter, an optical light detector, an encryption module, or an electrochemical module configured to interpret signals generated at electrodes within the test card.

6. The analytical device of claim 1, wherein the data gathering and processing element comprises each of an optical module driver board, and electrochemical module driver board, an optical filter, an optical light detector, an encryption module, and an electrochemical module configured to interpret signals generated at electrodes within the test card.

7. The analytical device of claim 1, wherein the signal readout system is configured to measure the fluid with fluorimetry.

8. The analytical device of claim 1, wherein one or more optical modes of measuring the fluid comprise a plurality of optical modes.

9. The analytical device of claim 1, wherein the instructions specify optical cells available on the analytical chip and which wavelengths to use to measure the fluid.

10. The analytical device of claim 1, wherein the signal readout system comprises:
a source of light,
an optical detector positioned to align with a proximal end of a microfluidic analytical chip card inserted into the receptacle and forming the pump-free microfluidic system.

11. The analytical device of claim 10, wherein the signal readout system comprises one or more optical filters configured to modify an optical beam in a beam path between the source of light and the optical detector.

12. The analytical device of claim 11, wherein the optical filters are configured to affect polarization of the optical beam.

13. The analytical device of claim 1, wherein the signal readout system comprises an electrochemical module driver board configured to detect an analytical signal generated by an electrochemical analysis chamber of the pump-free microfluidic system.

14. The analytical device of claim 1, wherein the signal readout system is configured to encrypt of data from a subset of optical pathways present in the test card.

15. The analytical device of claim 1, wherein:
the chemical modification of the surface comprises a functionalization process to introduce oxygen-containing molecules to the surface.

16. The analytical device of claim 15, wherein:
the chemical modification comprises a region of the substrate previously subjected to plasma-based surface modification leaving products of reactions between plasma species and plasma-broken chemical bonds in the region.

17. The analytical device of claim 1, comprising:
the pump-free microfluidic system, wherein the pump-free microfluidic system comprises a chip having a substrate that comprises a plurality of microfluidic channels each with a surface functionalized to promote self-flow of a fluid without any internal or external pumping.

18. The analytical device of claim 17, wherein:
the first substrate is plastic;
the plurality of microfluidic channels are a mask-less, plasma-defined pattern on the surface; and
the surface is a surface of the plastic.

19. The analytical device of claim 1, wherein:
the sample analysis element is part of the pump free microfluidic system; and
the signal readout system comprises each of an electrochemical analysis chamber, an optical analysis chamber, a biomaterial analysis chamber, and a spectrophotometry chamber.

* * * * *